United States Patent [19]

Lincoln et al.

[11] Patent Number: 5,103,016

[45] Date of Patent: Apr. 7, 1992

[54] PHOTOGRAPHICALLY USEFUL COMPOUNDS

[75] Inventors: David G. Lincoln, Webster; Mark J. Robbins, Rochester, both of N.Y.

[73] Assignee: Eastman Kodak Company, Rochester, N.Y.

[21] Appl. No.: 678,776

[22] Filed: Apr. 1, 1991

Related U.S. Application Data

[62] Division of Ser. No. 542,621, Jun. 25, 1990, Pat. No. 5,061,799.

[51] Int. Cl.$^5$ ................ C07D 249/14; C07D 249/12
[52] U.S. Cl. ............................................. 548/263.8
[58] Field of Search ................................. 548/263.8

[56] References Cited

U.S. PATENT DOCUMENTS

| | | | |
|---|---|---|---|
| 2,444,605 | 7/1948 | Heimbach et al. | 95/7 |
| 2,566,659 | 9/1951 | Fry | 95/7 |
| 2,837,521 | 6/1958 | Burns | 260/256.4 |
| 2,933,388 | 4/1960 | Knott | 96/7 |
| 3,202,512 | 8/1965 | Williams | 96/109 |
| 4,728,601 | 3/1988 | Rowland et al. | 430/565 |

*Primary Examiner*—Patricia L. Morris
*Attorney, Agent, or Firm*—L. George Legg

[57] ABSTRACT

A multi-step process for the preparation of tetraazaindenes provides new, intermediate compounds and methods for their formation. A first method or step (1) of the process comprises reacting Meldrum's acid (cyclic dimethylmethylene malonate) or a related compound with an orthoester to form a first intermediate. Another method or step (2) of the invention comprises reacting the first intermediate with a triazole to form a second intermediate. A third method or step (3) comprises reacting the second intermediate with a base to form a tetraazaindene salt from which the tetraazaindene can then be formed. Other methods of the invention comprise sequential combinations of the three new methods above described. For example, Meldrum's acid is reacted with triethylorthoacetate in the presence of pyridine and ethyl acetate to form a first intermediate represented by the structural formula

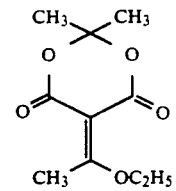

The first intermediate is then reacted with 3-amino-5-methylthio-1,2,4-triazole to form a second intermediate represented by the structural formula

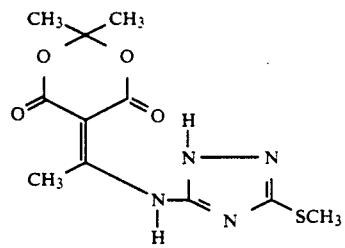

Upon reaction with sodium carbonate, a tetraazaindene having the formula

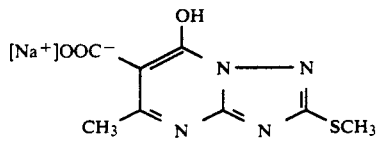

is produced. Other related compounds are formed when reactants related to those set forth above are employed. Tetraazaindenes are useful as photographic chemicals, for example, as image toners or stabilizers in photographic emulsions.

4 Claims, 1 Drawing Sheet

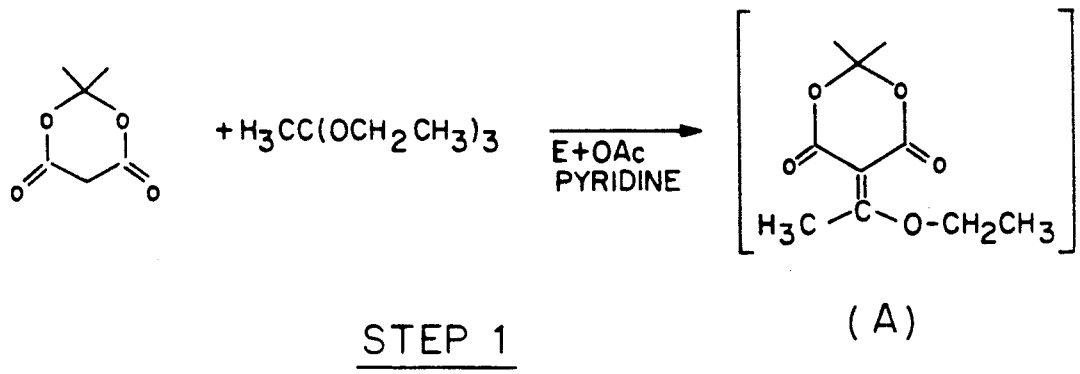
STEP 1
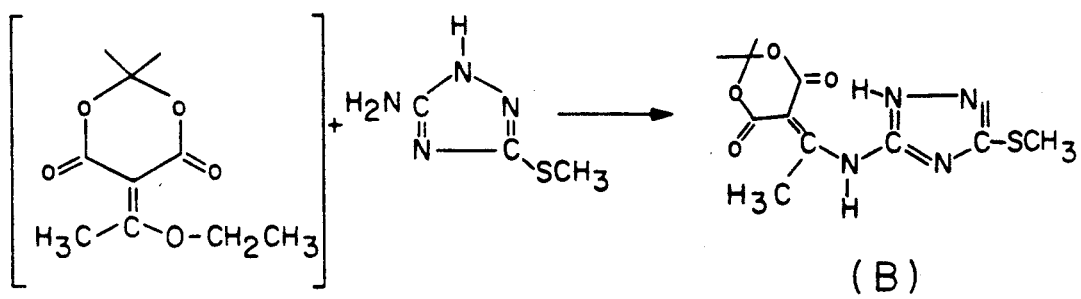
STEP 2
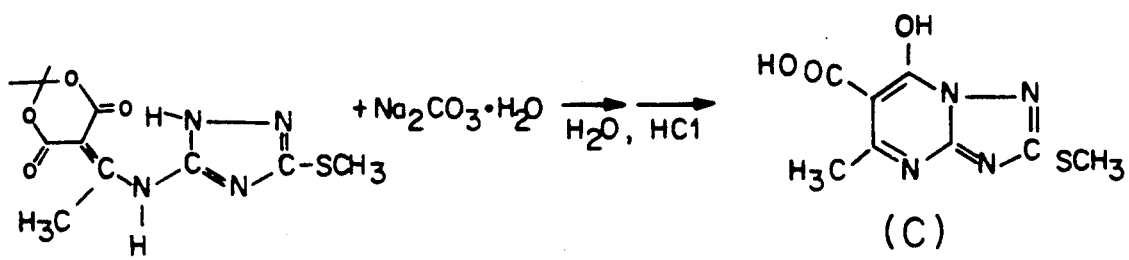
STEP 3

PHOTOGRAPHICALLY USEFUL COMPOUNDS

CROSS REFERENCE APPLICATION

This application is a division of application Ser. No. 542,621, filed June 25, 1990, now U.S. Pat. No. 5,061,799.

FIELD OF THE INVENTION

This invention relates to an improved method for the preparation of tetraazaindenes and to intermediate compounds prepared for use therein.

BACKGROUND OF THE INVENTION

It is known that tetraazaindenes and their salts represented by the general structural formula

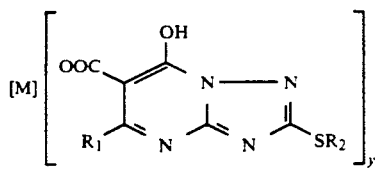

I wherein M is a metal cation selected from Group IA and IIA metals and y is the valence of the metal cation, are useful as stabilizers in photographic emulsions. For example, it is known that in a silver halide emulsion there is a detectable amount of the silver salt reduced during development in the unexposed areas. The result can be degradation of the photographic image. It is well known that the presence of tetraazaindenes in the silver halide emulsion can decrease the degradation of the developed photographic image. Accordingly, there has been considerable effort expended in the art to prepare tetraazaindene compounds.

Prior workers have shown that the preparation of tetraazaindenes is not an easy task. Several approaches have been taken by prior workers to overcome this problem.

One prior art approach ("prior art approach 1") to prepare tetraazaindenes is by the condensation of a β-keto ester, a malonic ester or a mononitrile of a malonic ester, with a 3-amino-1,2,4-triazole. One problem with this approach is that preparation of the β-keto ester for the reaction can be inefficient in regard to yield and the β-keto ester can decompose and consequently result in a reduced overall reaction product yield. Another problem is that the time involved for the reaction to yield a commercial amount of tetraazaindene is lengthy and thus involves a significant manufacturing process cost. A third problem is that undesirable intermediate compounds that are unstable and difficult to isolate are formed, necessitating an additional purification step or steps and negatively effecting the process times, cost, and yield.

Another prior art approach ("prior art approach 2") is to condense a triazole or a polyazole having at least one primary amino group with a β-keto ester, a β-keto acetal, a cyclic β-keto ester, or a malonic or cyanacetic ester. This approach likewise has all the above-stated problems that can result in increased process times and costs and decreased yield of tetraazaindenes.

A third prior art approach ("prior art approach 3") results in a tetraazaindene having a carboxyl group by deesterification of the tetraazaindene, said tetraazaindene having been prepared by condensing an alkoxymethenemalonic acid ester with a 3-amino-1,2,4-triazole compound under alkaline conditions. The free acid form is obtained by acidification of the deesterified tetraazaindene. This process not only has the above-described problems of the prior art processes but it involves the additional process step of deesterification followed by acidification, thus further increasing the process time, process steps, and process costs.

This invention solves the prior art problems noted above. It does not generate unstable and difficult to isolate intermediate compounds. Instead, intermediates are produced that react faster and more completely, thus eliminating the costly and time-consuming step or steps of isolation and purification associated with unstable intermediate compounds.

Furthermore, the reaction conditions of this invention are milder and result in increased yield of the tetraazaindene. Also, the reactions take place faster and thus involve decreased process costs. Thus, by means of this invention, there is provided an improved, three-step synthesis of tetraazaindenes that solves the above-stated prior art problems.

RELATED ART

U.S. Pat. No. 2,444,605 (prior art approach 1) discloses photographic silver halide emulsions containing tetraazaindenes prepared by condensation of a β-keto ester, a malonic ester or a mononitrile of a malonic ester, with a 3-amino-1,2,4-triazole.

U.S. Pat. No. 2,566,659 (prior art approach 2) discloses photographic silver halide emulsions containing tetraazaindenes prepared by reacting 2-amino-5-methylmercapto-1,3,4-triazole or a 2-amino-5-mercapto-1,3,4-triazole with a β-ketonic ester, a cyclic β-keto ester, or a malonic or cyanacetic ester.

U.S. Pat. No. 2,837,521 (prior art approach 2) discloses a process for preparing polyazaindene compounds by condensing β-ketoacetals and polyazole compounds having at least one attached primary amino group.

U.S. Pat. No. 2,933,388 discloses tetraazaindenes prepared by the condensation of 3-amino-1,2,4-triazoles with acylacetic esters.

U.S. Pat. No. 3,202,512 (prior art approach 3) discloses photographic silver halide emulsions containing tetraazaindenes prepared by the condensation of alkoxymethylenemalonic acid ester with a 3-amino-1,2,4-triazole under alkaline conditions is unstable and not easily isolable. The reference discloses that the tetraazaindene compound having a carbalkoxyl group can be deesterified to a carboxyl group. The free acid can then be obtained by acidification. The patent also discloses that the carboxylated tetraazaindene may be acidified to prepare the free acid form.

U.S. Pat. No. 4,728,601 (prior art approach 1) discloses the preparation of ballasted tetraazaindenes by reacting a triazole with a β-keto ester.

BRIEF DESCRIPTION OF THE DRAWING

The drawing illustrates a sequence of reactions in the process of this invention. According to convention, methyl groups are not shown at the end of the unsatisfied valence lines. Also, in the drawings, "EtOAc" is ethyl acetate. Three reactions are illustrated and are labelled steps, 1, 2 and 3, and correspond to Examples 1, 2, and 3, respectively, in the specification. The compounds dimethyl-5-(1-ethoxyethylidene)-2,2-1,3-Dioxane-4,6-Dione and 2,2-dimethyl-5-(1-((5-(methylthio)-

1H-1,2,4-triazol-3-yl)amino)ethylidene)-1,3-dioxane-4,6-dione formed in steps 1 and 2 and labelled "A" and "B" respectively in the drawing require no further purification or isolation steps. The end reaction product shown in step 3 and labelled "C" is 5-carboxy-4-hydroxy-6-methyl-2-(methylthio)-1,3,3A,7-tetraazaindene. The reaction product of step two is unstable and not easily isolable. The reaction products of steps 2 and 3 show good stability and product yield.

SUMMARY OF THE INVENTION

The invention provides a new method, more cost-efficient than prior art methods, for preparing the tetraazaindenes of Formula I. The new method comprises a multi-step process that includes new intermediate methods and compounds. The new intermediate compounds require no purification or isolation step but can be directly reacted to provide a good yield of tetraazaindene in comparison with the method of the prior art.

One of the new methods of the invention is a method, hereinafter referred to as step one, for preparing a novel first intermediate compound represented by the structural formula

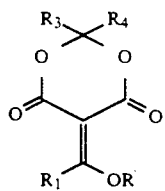

(II)

The method of step one comprises reacting a compound represented by the structural formula

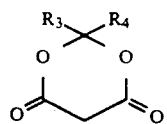

IV wherein $R_3$ and $R_4$ are independently selected from alkyl groups having up to about 4 carbon atoms with an orthoester represented by the structural formula $R_1-C(OR)_3$ wherein R is an alkyl group having up to about 4 carbon atoms and $R_1$ is selected from straight chain alkyl groups and aryl groups having up to about 8 carbon atoms to form the first intermediate of Formula II. The reaction of step one takes place in the presence of (a) a catalytic amount of a tertiary amine having a pKa sufficient to catalyze the reaction and (b) a substantially anhydrous organic solvent.

Another of the new methods of the invention is a method, hereinafter referred to as step two, for preparing a novel second intermediate compound represented by the structural formula

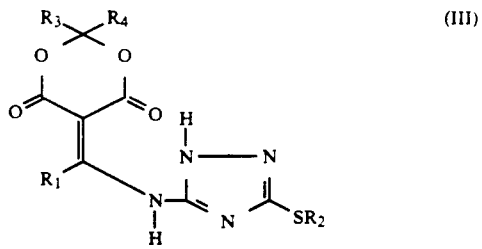

(III)

wherein $R_2$ is an alkyl or aryl group having up to about 8 carbon atoms and $R_1$, $R_3$, and $R_4$ are as described above. The method of step two comprises reacting the new first intermediate compound of Formula II with a triazole represented by the structural formula

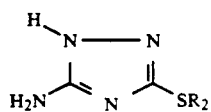

to form a composition containing the compound of Formula III.

A third method of the invention, hereinafter referred to as step three, comprises reacting the new second intermediate compound of Formula III with a base to form a tetraazaindene salt represented by the structural formula

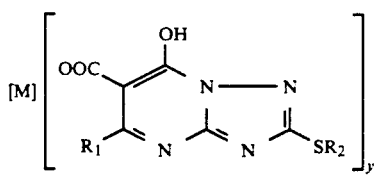

I wherein M is a metal cation selected from Group IA and IIA metals and y is the valence of the metal cation. In a preferred embodiment, hereinafter referred to as step four, an acid is added to the tetraazaindene salt of Formula I to form the tetraazaindene by substituting a hydrogen or hydrogens for M, thereby forming a carboxyl group (COOH) on each such tetraazaindene group.

Another method of the invention comprises a sequential combination of step one and step two described above, that is, starting with the reactants of step one and forming the intermediate compound of Formula II which is then reacted as described in step two to form the intermediate compound of Formula III.

In another method of the invention, a sequential combination of step two and step three described above form the compound of Formula I starting with the reactants of step two.

Another method of the invention comprises a sequential combination of steps one, two, and three to form the compound of Formula I.

In any of the stated methods of the invention that form the compound of Formula I, step four described above may then be conducted to form the related tetraazaindene.

The methods of this invention are conducted at reaction conditions such as pH and temperature and the like that produce a good yield and product stability for the individual or sequential step method. The tetraazaindenes thus produced are useful as image toners or stabilizers in silver halide photographic emulsions to improve the exposed film resistance to fogging and the like. Tetraazaindenes generally are manufactured, packaged and stored in the crystalline form. The tetraazaindene may then be rendered water-soluble by conversion to the salt to facilitate its use in manufacturing photographic emulsions.

DESCRIPTION OF PREFERRED EMBODIMENTS

A preferred method of the invention, hereinafter referred to as step one, comprises the preparation of a compound represented by the structural formula

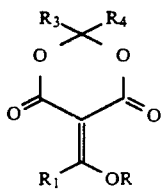

wherein R is an alkyl group having up to about 4 carbon atoms, $R_1$ is selected from straight chain alkyl groups and aryl groups having up to about 8 carbon atoms, and $R_3$ and $R_4$ are independently selected from alkyl groups having up to about 4 carbon atoms, by reacting a compound represented by the structural formula

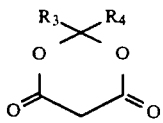

wherein $R_3$ and $R_4$ are as above-described with an orthoester represented by the structural formula $R_1$—C—(OR)$_3$ wherein R and $R_1$ are as above-described, in the presence of a) a catalytic amount of a tertiary amine having a pKa sufficient to catalyze the reaction, and b) a substantially anhydrous organic solvent, to form said compound II. In a preferred embodiment, $R_3$ and $R_4$ are both methyl.

In another preferred embodiment of the invention, hereinafter referred to as step two, a compound of Formula II is reacted with a triazole represented by the structural formula

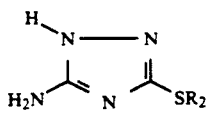

wherein $R_2$ is an alkyl or aryl group having up to about 8 carbon atoms to form a composition containing a compound of Formula III. In a preferred embodiment of the compound of Formula III, $R_1$ and $R_2$ are each a straight chain alkyl group of up to about 8 carbon atoms.

In yet another preferred embodiment of the invention, hereinafter referred to as step three, a compound of Formula III is reacted with a base to form a tetraazaindene salt represented by Formula I.

Another preferred embodiment of the invention is a sequential combination of steps one and two to form a compound of Formula II. Another preferred embodiment is a sequential combination of steps two and three to form a compound of Formula I.

A particularly preferred embodiment comprises a sequential combination of steps one, two and three to form a compound of Formula I. For example, a particularly preferred tetraazaindene salt of Formula I comprises both $R_1$ and $R_2$ as methyl groups and X as hydrogen. In accordance with such preferred embodiment, in the multi-step process of the invention, cyclic dimethylmethylene malonate, commonly known and referred to by those skilled in the art as Meldrum's acid, is a preferred reactant wherein both $R_3$ and $R_4$ are methyl in Formula IV of step one. Meldrum's acid is a readily available and cost-effective compound, and is prepared by methods well-known in the art. See, for example, Meldrum, J. Chem. Soc., 93, 598 (1908); see also "Organic Reactions," John Wiley and Sons, Inc., New York, N.Y., 1946, Vol. III, p. 124. In practicing the broader scope of the invention, the preparation of compounds related to Meldrum's acid by employing related starting materials is also well within the skill of the art.

A preferred orthoester of formula $R_1$—C(OR)$_3$ in step one comprises triethylorthoacetate wherein $R_1$ is methyl and R is ethyl. In a particularly preferred embodiment, Meldrum's acid is reacted with triethylorthoacetate to form the compound of Formula II wherein $R_1$ is methyl, R is ethyl, and $R_3$ and $R_4$ are both methyl.

Preferred tertiary amines in step one include triethylamine, polyvinylpyridine, and 1,8-diazabicyclo-(5.4.0)undec-7-ene. A particularly preferred tertiary amine in step one is pyridine. The tertiary amine employed as the catalyst in step one should be used in a catalytic amount and having a pKa sufficient to catalyze the reaction of step one. It is within the skill of one of ordinary skill in the art of organic chemistry or the art of organic compound synthesis to determine the amount of tertiary amine to use as the catalyst and to determine the pKa of the tertiary amine sufficient to catalyze the reaction. For example, the selected catalytic amount of tertiary amine can be dependent on the particular reactants of the invention that are selected and also can be dependent on the weight quantities of the reactants. Thus, as the weights of the reactants of step one are increased the catalyst amount of tertiary amine will also increase. A preferred weight proportion of tertiary amine to the reactant having the formula $R_1$—C(OR)$_3$ as defined hereinabove can be in the range of about 0.01:1 to about 0.2:1 with respect to either reactant. Generally, a catalytic amount of tertiary amine can comprise an amount nearer the low end of the range if it has a pKa higher than a tertiary amine of the invention requiring a higher catalytic amount within the above range. For example, when the tertiary amine comprises pyridine of a pKa of about 5.2, and the reactants are triethylorthoacetate and 2,2-Dimethyl-m-dioxane-4,6-dione in the respective weight proportion of about 1.12:1, then a catalytic amount of the pyridine can comprise a relative weight proportion to the respective two reactants above of about 0.09:1.12:1 respectively.

Likewise, the pKa of the tertiary amine sufficient to catalyze the reaction is within the skill of one of ordinary skill in the art and can be determined without undue experimentation for the particular reactants of the invention selected and for a selected reaction condition as set forth herein. A preferred pKa is about 5 to about 7.

A preferred anhydrous solvent in step one is toluene and a particularly preferred anhydrous solvent is ethyl acetate. Other anhydrous solvents such as methylene chloride and acetic acid may be employed but do not provide as good reaction times and product yield because the above stated such preferred solvents have a polar character and have sufficient solvent power to produce good reaction times and product yield for the step one reaction. The use of methylene chloride also involves environmental concerns with atmospheric emissions and the related economic costs.

The reaction of step one preferably takes place at a temperature of from about 0° C. to about 50° C. A particularly preferred reaction temperature is about 50° C. A preferred reaction pressure is ambient pressure although step one can be conducted at a pressure from below ambient pressure to about 100 psig.

In step two, a preferred triazole is 3-amino-5-methylthio-1,2,4-triazole. For example, the preferred triazole can be reacted with a Formula II compound wherein $R_1$ is methyl and R is ethyl to form a composition containing a compound of Formula III wherein $R_3$ and $R_4$ are both methyl and $R_1$ and $R_2$ are both methyl.

It is preferable to carry out the reaction of step two in the same solvent as step one although a different but appropriate solvent can be readily selected by the skilled practitioner.

In step two, the reaction preferably takes place at a temperature of from about 0° C. to about 25° C. A particularly preferred reaction temperature is about 25° C. A preferred reaction pressure is ambient pressure although step three can be conducted at a pressure from below ambient pressure to about 100 psig.

A preferred base in step three is a Group IA or IIA metal hydroxide or carbonate. Particularly preferred bases include sodium hydroxide, potassium hydroxide, ammonium hydroxide, sodium carbonate, potassium carbonate, and mixtures thereof. A preferred reaction pH is about 9. In a particularly preferred embodiment of step three, a compound of Formula III wherein $R_3$ and $R_4$ are both methyl and $R_1$ and $R_2$ are both methyl is reacted with sodium carbonate to form a compound of Formula I wherein $R_1$ and $R_2$ are both methyl, M is sodium, and y has a value of one.

Step three is conducted in an aqueous solution whereas step one and step two are conducted under substantially anhydrous conditions in order to maximize the product yield for the particular step. In a preferred embodiment, ethyl acetate is dried with magnesium sulfate and then employed as the solvent in step one and step two. This expedient is exemplified in Example 1.

In step three, the reaction preferably takes place at a temperature of from about 0° C. to about 50° C. A particularly preferred reaction temperature is about 50° C. A preferred reaction pressure is ambient pressure although step three can be conducted at a pressure from below ambient pressure to about 100 psig.

The reaction time for each of the steps of the process of the invention is not a truly independent variable and is dependent at least to some extent on the inherent reactivity of the reactants of the step and also in the reaction temperature for the step. In general, the higher the temperature and the more active the reactants employed, the shorter the reaction time. Thus, the time of reaction is not critical so long as it is sufficient for reaction to take place. In general, the multi-step process is complete in about 8 to about 16 hours. The time of reaction for each step can be readily determined by a skilled practitioner using known techniques.

The amount of solvent employed is not critical. In general, one employs enough solvent to dissolve the product(s) and reactant(s) to an appreciable extent. There is no real upper limit on the amount of solvent employed. This is generally influenced by the size of the reaction vessel, process economics, and similar secondary considerations.

As stated hereinabove, it is not necessary that the same solvent be present throughout the process. For example, after step one, one may change solvents prior to resuming step two. Thus, for example, one may wish to change the solvent (a) because it is too volatile at an increased reaction temperature used at a latter stage of the process, or (b) when the solvent becomes incapable of dissolving the product being produced.

Step one and step two in the process of this invention are conducted in the substantial absence of water, that is, under substantially anhydrous conditions. The product yield of step one and step two is thereby optimized and step one and step two are therefore each more commercially viable. For example, if the moisture content of the orthoester of formula $R_1-C(OR)_3$ of step one as defined above is above the preferred limits as set forth herein (infra) then the reactant of Formula IV as defined above can decompose, thus lowering the product yield of step one. Stated another way, a skilled practitioner (familiar with the aromatic reactions such as substitution, addition and/or ring closures) will appreciate that step one and step two of the process of this invention are conducted under substantially dry conditions in order to improve the yield of desired product. For example, an operator may wish to employ ethyl acetate as the solvent in the multi-step process of this invention, and prior to using it the operator may proceed to dry the solvent with magnesium sulfate. Preferably, the water content is less than about 0.5 weight percent. It is particularly preferred that the water content is less than about 0.1 weight percent. It is, however, preferable to conduct step three in an aqueous solution. This multi-step expedient is exemplified in the examples.

In any of the above-described methods of the invention that result in forming a compound of Formula I, a preferred embodiment is to conduct an additional step, hereinafter referred to as step four, in which compound I is reacted with an acid to form a tetraazaindene by substituting a hydrogen or hydrogens for M, thereby forming a carboxyl group (COOH) on each such tetraazaindene group.. A preferred acid is hydrochloric acid and a preferred reaction pH is about 1.

All preferred conditions, reagents, etc, for the above-described sequential step methods are the same as those recited previously in the detailed description, hereinabove, of those steps as individual inventive methods.

The following Examples are presented to further illustrate some preferred embodiments of the invention.

(Where quantities, below, are expressed as "parts" this means parts by weight.)

EXAMPLE 1

Preparation of dimethyl-5-(1-ethoxyethylidene)-2,2-1,3-dioxane-4,6-dione

A suitable vessel was placed on a nitrogen purge and 938 parts of ethyl acetate was introduced and stirred. A quantity of 22.68 parts of magnesium sulfate was then added to the vessel and the contents were stirred for 15 minutes at 25° C.

The ethyl acetate was then removed and dried by twice circulating the vessel contents through a filter press, after which the dried ethyl acetate was introduced back to the vessel. A sample of the ethyl acetate showed a water content of less than 0.1 weight percent. A quantity of 250 parts of 2,2-Dimethyl-m- dioxane-4,6dione was then added to the vessel. By vacuum suction 281 parts of triethylorthoacetate was then introduced to the vessel. 22.6 parts of pyridine was then added to the vessel and a nitrogen purge placed on the vessel. The contents of the vessel were then heated to 50° C. and stirred for 2 hours. Fourier Transform Infrared Spectroscopy (FTIR) demonstrated the reaction mixture contained dimethyl-5-(1-ethoxy-ethylidene)-2,2-1,3-dioxane-4,6-dione.

EXAMPLE 2

Preparation of 2,2-dimethyl-5-(1-((5-(methylthio)-1H1,2,4-triazol-3-yl)amino)ethylidene)-1,3-dioxane-4,6dione The method of Example 1 was carried out and a suitable vessel was charged with the dimethyl-5-(1-ethoxyethylidene)-2,2-1,3-dioxane-4,6-dione product of Example 1 and 156 parts of 3-amino-5-(methylthio)-1,2,4-triazole. The reaction mixture was stirred at 25° C. for 1 hour, cooled to 5° C., and stirred at 5° C. for 1 hour.

To a second vessel dry, and on a nitrogen purge, was introduced 446 parts of isopropyl alcohol which was then stirred at 0° C.

The reaction mixture of the first vessel was then centrifuged and the precipitate was washed with the isopropyl alcohol. The reaction product was dried at 30° C. High pressure liquid chromatography, nuclear magnetic resonance method, and mass spectrometry analysis demonstrated the reaction product was 2,2-dimethyl-5-(1-((5-methylthio)-1H-1,2,4-triazol-3-yl)amino)-ethylidene)-1,3-dioxane-4,6-dione. The yield was about 250 parts or 70% maximum theoretical yield.

EXAMPLE 3

Preparation of 5-carboxy-4-hydroxy-6-methyl-2-(methylthio)-1,3,3A,7-tetraazaindene The method of Example 2 was carried out to produce 250 parts of 2,2-dimethyl-5-(1-((5-methyl- thio)-1H-1,2,4-triazol-3-yl)amino)ethylidene)-1,3-dioxane-4,6-dione. A suitable vessel was placed on a nitrogen purge and 1000 parts of distilled water was added to the vessel. 105 parts of sodium carbonate was added to the vessel and the contents stirred at 40° C.

The 250 parts of 2,2-dimethyl-5-(1-((5-methylthio)-1H-1,2,4-triazol-3-yl)amino)ethylidene)-1,3-dioxane-4,6-dione was introduced to the vessel and the reaction mixture was stirred at 50° C. for 30 minutes. The reaction mixture was filtered and then stirred while cooling to 5° C.

Hydrochloric acid was then added to the reaction mixture, lowering the pH to 1 and resulting in a thick slurry. The slurry was stirred at 5° C. for 30 minutes, and the reaction product was then collected by centrifuge. The reaction product was washed with filtered, cold water and then dried at 60° C. High pressure liquid chromatography, nuclear magnetic resonance method, and mass spectrometry analysis showed the reaction product was 5-carboxy-4-hydroxy-6-methyl-2-(methylthio)-1,3,3A,7-tetraazaindene. The yield was 185 parts or 92% maximum theoretical yield. In terms of the sequential process of conducting step one, then step two, and then step three with the reactants specified in Example 3, the overall process yield was 64.3% of the maximum theoretical yield.

The invention has been described in detail with particular reference to preferred embodiments thereof, but it will be understood that variations and modifications can be effected within the spirit and scope of the invention.

We claim:

1. A compound represented by the structural formula

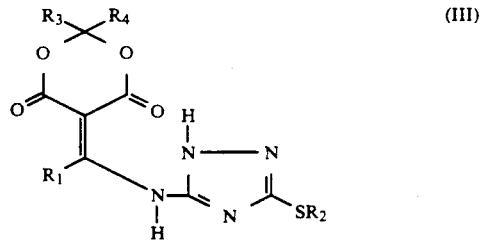

(III)

wherein
$R_1$ is selected from straight chain alkyl groups and aryl groups having up to about 8 carbon atoms,
$R_2$ is an alkyl or aryl group having up to about 8 carbon atoms, and
$R_3$ and $R_4$ are independently selected from alkyl groups having up to about 4 carbon atoms.

2. The compound of claim 1 wherein both $R_3$ and $R_4$ are methyl.

3. The compound of claim 1 wherein $R_1$ and $R_2$ each are a straight chain alkyl group of up to about 8 carbon atoms.

4. The compound of claim 1 wherein $R_1$ and $R_2$ are methyl and $R_3$ and $R_4$ are methyl.

* * * * *